United States Patent
Chiu et al.

(10) Patent No.: US 7,217,515 B2
(45) Date of Patent: May 15, 2007

(54) HURP GENE AS A MOLECULAR MARKER FOR BLADDER CANCER

(75) Inventors: Allen W. Chiu, Yung Kang (TW);
Yu-Lun Huang, Yung Kang (TW);
Chen-Kung Chou, Yung Kang (TW)

(73) Assignee: Chi Mei Foundation Medical Center, Tainan (TW)

( * ) Notice: Subject to any disclaimer, the term of this patent is extended or adjusted under 35 U.S.C. 154(b) by 555 days.

(21) Appl. No.: 10/259,326

(22) Filed: Sep. 30, 2002

(65) Prior Publication Data

US 2004/0072166 A1 Apr. 15, 2004

(51) Int. Cl.
*C12Q 1/68* (2006.01)
*C12P 19/34* (2006.01)

(52) U.S. Cl. .................. 435/6; 435/91.1; 435/91.2
(58) Field of Classification Search .................. None
See application file for complete search history.

(56) References Cited

U.S. PATENT DOCUMENTS

| | | | |
|---|---|---|---|
| 6,251,638 B1 | 6/2001 | Umansky et al. | |
| 6,287,820 B1 | 9/2001 | Umansky et al. | |
| 6,291,163 B1 | 9/2001 | Sidransky | |
| 6,335,167 B1 | 1/2002 | Pinkel et al. | |
| 6,335,170 B1 | 1/2002 | Orntoft | |
| 6,376,188 B1 | 4/2002 | Halling et al. | |
| 2003/0027171 A1* | 2/2003 | Yang et al. | 435/6 |
| 2004/0058340 A1* | 3/2004 | Dai et al. | 435/6 |

FOREIGN PATENT DOCUMENTS

| | | | |
|---|---|---|---|
| JP | 2004248508 A * | 9/2004 | |
| WO | WO 99/63110 | 12/1999 | |
| WO | WO 01/86288 | 11/2001 | |
| WO | WO 02/27329 | 4/2002 | |
| WO | WO 2003016465 A2 * | 2/2003 | |

OTHER PUBLICATIONS

Sequence Homology Report.*
Anderson et al., "A comparison of selected mRNA and protein abundances in human liver," Electrophoresis, 1997, vol. 18, pp. 533-537.*
mRNA level and protein correlation?, Roychowdhury, H.S. [posted Mar. 2004] [online], [retrieved on Jul. 8, 2006] Retrieved from BIONET using Internet <URL:http://www. bio.net/bionet/mm/methods/2004-March/097973.html>.*
Gu et al., "Dysregulation of TAp63 mRNA and Protein Levels in Psoriasis," 2006, Journal of Investigative Dermatology, vol. 126, pp. 137-141.*
"Potential Molecular Marker for Detecting Transitional Cell Carcinoma", Chiu et al.; Urology 60(1), Elsevier Science Inc. 2002, pp. 181-185.

"Urine Based Markers of Urological Malignancy" Konety et al.; The Journal of Urology vol. 165, pp. 600-611, Feb. 2001.
"The World Health Organization/International Society of Urological Pathology Consensus Classification of Urothelial (Transitional Cell) Neoplasms of the Urinary Bladder", Epstein et al.; The American Journal of Surgical Pathology 22(12) 1998; 1435-1448.
"Characterization of a Novel Human Cell-Cycle-Regulated Homologue of Drosophila dig1"; Bassal et al.; Genomics vol. 77, No. 1-2, Sep. 2001, pp. 5-7.
"Clinical Evaluation of the BTA TRAK Assay and Comparison to Voided Urine Cytology and the Bard BTA Test in Patients With Recurrent Bladder Tumors"; Ellis et al.; Urology 50(6); Elsevier Science Inc. 1997, pp. 882-887.
"Improved Detection of Recurrent Bladder Cancer Using the Bard BTA stat TEST"; Sarosdy et al.; Urology 50(3), Elsevier Science Inc. 1997, pp. 349-353.
"Sensitive Detection of Transitional Cell Carcinoma of the Bladder by Microsatellite Analysis of Cells Exfoliated in Urine"; Seripa et al., Int. J. Cancer (Pred. Oncol.): 95, pp. 364-369 (2001).
"Screening and Monitoring for Bladder Cancer: Refining the Use of NMP22", Ponsky et al.; The Journal of Urology vol. 166, 75-78 Jul. 2001, pp. 75-78.
"Detection of Bladder Cancer Using a Novel Nuclear Matrix Protein, BLCA-4[1]" Clinical Cancer Research vol. 6, Jul. 2000, 2618-2625.
"Urinary Cytokeratin 20 as a Marker for Transitional Cell Carcinoma", Rotem et al., Eur. Urol 2000:37, pp. 601-604.
"Evaluation of Two New Urinary Tumor Markers: Bladder Tumor Fibronectin and Cytokeratin 18 for the Diagnosis of Bladder Cancer[1]"; Sanchez-Carbayo et al.; Clinical Cancer Research vol. 6, Sep. 2002, pp. 3585-3594.
"Urinary Tissue Polypeptide-Specific Antigen for the Diagnosis of Bladder Cancer" Sanchez-Carbayo et al.; Urology 55(4), Elsevier Science Inc. 2000, pp. 526-532.
"Urine Detection of Survivin and Diagnosis of Bladder Cancer" Smith et al., JAMA, vol. 285, No. 3, Jan. 17, 2001, pp. 324-328.

* cited by examiner

*Primary Examiner*—Young J. Kim
(74) *Attorney, Agent, or Firm*—Foley & Lardner LLP (57) ABSTRACT

Hepatoma up-regulated protein (HURP) gene serves as a useful molecular marker in the detection, preliminary screening and monitoring of bladder cancer in a human subject. A method for the detection of bladder cancer, in particular transitional cell carcinoma (TCC) of the bladder, in a human subject is disclosed, in which the detected expression of the human HURP gene in a sample taken from a subject suspected to have bladder cancer is indicative of the presence of the bladder cancer. The present invention further provides a non-invasive method for the detection, preliminary screening or monitoring of urinary TCC in a suspected subject, in which a urine sample taken from the subject is analyzed to determine an expression of the human HURP gene, the presence of which is indicative of the presence of urinary TCC.

22 Claims, 5 Drawing Sheets

HURP full length (from AB076695. Homo sapiens mRNA...[gi:21321251])

```
agcaaaccaa tcgcaagcct cgttgagtgg aaggggtggg atcttccccg gaagtttgg    60
ttaaagcccc tccaatcagc ggctcggtgc ggcaagtttg aatttcgtgg aggctcgggt   120
tgtgagggtt cctgcttcgg agtcggcggt ggtcgtccag accgagtgtt ctttactttt   180
tgtttggttg aggttcacg ctagaaggtg gctcaggatg tcttcatcac atttgccag    240
tcgacacagg aaggatataa gtactgaaat gattagaact aaaattgctc ataggaaatc   300
actgtctcag aaagaaaata gacataagga atacgaacga aatagacact ttggtttgaa   360
```
F primer of 1st primer pair            5'-ggatcc aatagacact ttggtttg-3'
                                              >>>>>>>>>>>>>>>>>>>>

```
agatgtaaac attccaacct tggaaggtag aattcttgtt gaattagatg agacatctca   420
agagcttgtt ccagaaaaga ccaatgttaa gccaagggca atgaaaacta ttctaggtga   480
tcaacgaaaa cagatgctcc aaaaatacaa agaagaaag caacttcaaa aattgaaaga   540
```
5'-caacgaaaa cagatgctc-3'       F primer of 2nd primer pair
   >>>>>>>>>>>>>>>>>>>

```
gcagagagag aaagctaaac gaggaatatt taaagtgggt cgttatagac ctgatatgcc   600
ttgttttctt ttatcaaacc agaatgctgt gaaagctgag ccaaaaaagg ctattccatc   660
ttctgtacgg attacaaggt caaaggccaa agaccaaatg gagcagacta agattgataa   720
cgagagtgat gttcgagcaa tccgacctgg tccaagacaa acttctgaaa agaaagtgtc   780
agacaaagag aaaaaagttg tgcagcctgt aatgcccacg tcgttgagaa tgactcgatc   840
```
R primer of 2nd primer pair                             3'-ctgagctag
                                                           <<<<<<<<<

```
agctactcaa gcagcaaagc aggttcccag aacagtctca tctaccacag caagaaagcc   900
tcgatgagt-5'
<<<<<<<<<
agtcacaaga gctgctaatg aaaacgaacc agaaggaaag gtgccaagta aaggaagacc   960
```
R primer of 1st primer pair  3'-cttgg tcttcctttc caccctagg-5'
                                <<<<<<<<<<<<<<<<<<<<<<

```
tgccaaaaat gtagaaacaa aacccgacaa gggtatttct tgtaaagtcg atagtgaaga  1020
aaatactttg aattcacaaa ctaatgcaac aagtggaatg aatccagatg gagtcttatc  1080
aaaaatggaa aacttacctg agataaatac tgcaaaaata aaagggaaga attccttcgc  1140
acctaaggat tttatgtttc agccactgga tggtctgaag acctatcaag taacacctat  1200
gactcccaga agtgccaatg cttttttgac acccagttac acctggactc ctttaaaaac  1260
agaagttgat gagtctcaag caacaaaaga aattttggca caaaaatgta aaacttactc  1320
taccaagaca atacagcaag attcaaataa attgccatgt cctttgggtc ctctaactgt  1380
ttggcatgaa gaacatgttt taaataaaaa tgaagctact actaaaaatt taaatggcct  1440
tccaataaaa gaagtcccat cacttgaaag aaatgaaggt cgaattgctc agccccacca  1500
tggtgtgcca tatttcagaa atatcctcca gtcagaaact gagaaattaa cttcacattg  1560
cttcgagtgg gacaggaaac ttgaattgga cattccagat gatgctaaag atcttattcg  1620
cacagcagtt ggtcaaacaa gactccttat gaaggaaagg tttaaacagt ttgaaggact  1680
ggttgatgat tgtgaatata acgaggtat aaaggagact acctgtacag atctggatgg  1740
attttgggat atggttagtt ttcagataga agatgtaatc cacaaattca acaatctgat  1800
caaacttgag gaatctgggt ggcaagtcaa taataatatg aatcataata tgaacaaaaa  1860
tgtctttagg aaaaaagttg tctcaggtat agcaagtaaa ccaaaacagg atgatgctgg  1920
aagaattgca gcgagaaatc gcctagctgc cataaaaaat gcaatgagag agagaattag  1980
gcaggaagaa tgtgctgaaa cagcagtttc tgtgatacca aaggaagtta ataaaatagt  2040
gttcgatgct ggattttca gagttgaaag tcctgttaaa ttattctcag gactttctgt  2100
ctcttctgaa ggcccttctc aaagacttgg aacacctaag tctgtcaaca agctgtatc  2160
tcagagtaga aatgagatgg gcattccaca acaaactaca tcaccagaaa atgccggtcc  2220
tcagaatacg aaaagtgaac atgtgaagaa gactttgttt ttgagtattc ctgaaagcag  2280
gagcagcata gaagatgctc agtgtcctgg attaccagat ttaattgaag aaaaccatgt  2340
tgtaaataag acagacttga aggtggattg tttatccagt gagagaatga gtttgcctct  2400
tcttgctggt ggagtagcag atgatattaa tactaacaaa aagaaggaa tttcagatgt  2460
tgtggaagga atggaactga attcttcaat tacatcacag gatgttttga tgagtagccc  2520
tgaaaaaaat acagcttcac aaaaatagcat cttagaagaa ggggaaacta aaatttctca  2580
gtcagaacta tttgataata aaagtctcac tactgaatgc caccttcttg attcaccagg  2640
tctaaactgc agtaatccat ttactcagct ggagaggaga catcaagaac atgccagaca  2700
catttcttt ggtggtaacc tgattacttt ttcacctcta caaccaggag aattttgaat  2760
ttaaaaataa atccaaacat tttccttcat attatcaatg cttatatatt ccttagacta  2820
ttgaaatttt ggagaaatg tatttgtgtt cacttctata gcatataatg ttttaatatt  2880
ctgtgttcat caaagtgtat ttagatata ctctttctca agggaagtgg ggatattttg  2940
tacattttca acacagaata aaaatgtac tgtgccttg                          2979
```

HURP GENE AS A MOLECULAR MARKER FOR BLADDER CANCER

BACKGROUND OF THE INVENTION

1) Field of the Invention

The present invention relates to the use of a human hepatoma up-regulated protein (HURP) gene as a molecular marker in the detection, preliminary screening or monitoring of bladder cancer in a human subject, in which the detected expression of the human HURP gene in a sample taken from a human subject suspected to have bladder cancer is indicative of the presence of the bladder cancer. The present invention thus provides an efficient method for the detection of bladder cancer, in particular transitional cell carcinoma (TCC) of the bladder, in a human subject. The present invention further provides a non-invasive method for the detection, preliminary screening or monitoring of urinary TCC in a human subject with high accuracy and convenience, in which a urine sample taken from a suspected human subject is analyzed to determine an expression of the human HURP gene, the presence of which is indicative of the presence of urinary TCC.

2) Description of the Related Art

Urothelial carcinoma is the second most common malignancy of the genitourinary tract and is also the second leading cause of death among all genitourinary tumors (Konety B R and Getzenberg R H: *Urine based markers of urological malignancy. J Urol* 165: 600–611, 2001). Transitional cell carcinoma (TCC) of the bladder is responsible for more than 90% of urothelial neoplasms and it either presents as papillary superficial lesions with low malignant potential or high grade tumors that can be invasive and lethal. When bladder cancer is detected early during a localized stage, the 5-year survival rate is 94%. Once the disease has spread regionally or distally, the 5-year survival rate drops to 49% and 6%, respectively (Droller M J: *Individualizing the approach to invasive bladder cancer. Contemp. Urol.*, July/August, pp. 54–61, 1990). It is thus important to detect the early events in the recurrence of superficial cancer before the cancer cells have time to change their behavior to invasive.

Classical cytology and cystoscopy under scheduled follow-up protocols are the main methods for the surveillance of patients with urinary TCC. The low sensitivity for low-grade tumor using voided urine cytology requires the frequent use of invasive cystoscopy, thus eliciting the associated discomfort and the potential risk of infection by urethral instrumentation during cystoscopy. The development of a sensitive noninvasive diagnostic test that could specifically detect bladder carcinoma in the early stages would improve the clinical outcomes by starting the treatment earlier.

U.S. Pat. No. 6,376,188, entitled "Method and probe set for detecting cancer," U.S. Pat. No. 6,251,638, entitled "Methods for detection of nucleic acid sequences in urine," and U.S. Pat. No. 6,287,820, entitled "Methods for protection of nucleic acid sequences in urine," disclosed the diagnosis of bladder cancer using sets of chromosomal probes to detect a urine sample, respectively.

U.S. Pat. No. 6,335,167, entitled "Comparative genomic hybridization (CGH)," disclosed the diagnosis of bladder cancer by detecting nucleic acid sequence copy numbers, in particular detecting an amplification of a unique sequence at least one position selected from the group consisting of q21 on human chromosome 8, q31-qter on human chromosome 13, p15-pter on human chromosome 7, q24-qter on human chromosome 8, cen-p13 on human chromosome 11 and q13-qter on human chromosome 9, in the test sample.

U.S. Pat. No. 6,291,163, entitled "Method for detecting cell proliferative disorders," disclosed the diagnosis of cancer (including bladder cancer) and pre-cancer in a subject, by detection of nucleic acid sequence, the features of which reside in the following steps: (a) amplifying test sample DNA at a genetic locus for which the subject is heterozygous, wherein the genetic locus comprises first and second alleles, said genetic locus comprising microsatellite DNA, wherein the test sample DNA is from a cell of an organ which drains into the test samples, wherein the test sample is selected from the group consisting of the subject's: urine, sputum, bile, stool, saliva, tears, serum and plasma; and (b) detecting an allelic imbalance at the genetic locus by determining and comparing level of microsatellite DNA present at the first allele to level of microsatellite DNA present at the second allele, wherein an allelic imbalance is indicative of cancer or precancer.

WO 01/86288, entitled "Method and apparatus for early diagnosis of bladder tumor in urine samples," disclosed a method for early diagnosis of bladder tumor in a urine sample, which comprises a step of amplification of the RNA extracted from cells present in the urine by using a marker for the messenger RNA of the catalytic component of telomerase (hTRT), a marker for β-actin to demonstrate RNA accessibility and as standard for quantitative estimation, in combination with at least one additional marker chosen from the group that comprises: a marker for a protein of the cytokeratin family, and a lymphocyte marker which is suitable to detect inflammatory cells associated with neoplastic infiltration, and a final step of detecting the amplified material.

WO 99/63110, entitled "Diagnosis and treatment of cancer," disclosed a method of diagnosing bladder cancer in a human patient comprising the steps of (i) obtaining a sample containing nucleic acid and/or protein from the bladder of a patient, preferably from the urothelium; and (ii) determining whether the sample contains a level of Pax 5 nucleic acid or protein associated with bladder cancer.

WO 02/27329, entitled "Biomarkers of transitional cell carcinoma of the bladder," disclosed protein markers, methods and kits that can be used as an aid for diagnosis of transitional cell carcinoma of the bladder (TCC) using markers that are differentially present in the samples of TCC patients and a control (e.g., subjects in whom TCC is undetectable).

U.S. Pat. No. 6,335,170 disclosed a method for determining an expression pattern of a urothelium or bladder cancer cell, comprising: determining expression of one or more genes in a sample comprising urothelium or bladder cancer cells, whereby a first pattern of expression is formed; subtracting from the first pattern of expression a second pattern of expression, wherein the second pattern was formed using the one or more genes and a sample comprising predominantly submucosal, smooth muscle, or connective tissue cells, said step of subtracting forming a third pattern of expression which reflects expression of the urothelium or bladder cancer cells independent of the proportion of submucosal, smooth muscle, or connective tissue cells present in the sample.

Other relevant studies directed to bladder cancer include: Konety B R and Getzenberg R H: Urine based markers of urological malignancy. J Urol 165: 600–611, 2001; Droller M J: Individualizing the approach to invasive bladder cancer. Contemp. Urol., July/August, pp. 54–61, 1990; Nomura N, Miyajima N, Sazuka T, et al: Prediction of the coding sequences of unidentified human genes. I. The coding sequences of 40 new genes (KIAA0001–KIAA0040) deduced by analysis of randomly sampled cDNA clones from human immature myeloid cell line KG-1. DNA Res 1: 27–35, 1994; Bassal S, Nomura N, Venter D, et al: Characterization of a novel human cell-cycle-regulated homologue of Drosophila dlg1. Genomics 77: 5–7, 2001; Ellis W J, Blumenstein B A, Ishak L M, et al: Clinical evaluation of the BTA TRAK assay and comparison to voided urine cytology and the Bard BTA test in patients with recurrent bladder tumors. The Multi Center Study Group. Urology 50: 882–887, 1997; Sarosdy M F, Hudson M A, Ellis W J, et al: Improved detection of recurrent bladder cancer using the Bard BTA stat Test. Urology 50: 349–353, 1997; Seripa D, Parrella P, Gallucci M, et al: Sensitive detection of transitional cell carcinoma of the bladder by microsatellite analysis of cells exfoliated in urine. Int J Cancer 95: 364–369, 2001; Ponsky L E, Sharma S, Pandrangi L, et al: Screening and monitoring for bladder cancer: refining the use of NMP22. J Urol 166: 75–78, 2001; Konety B R, Nguyen T S, Dhir R, et al: Detection of bladder cancer using a novel nuclear matrix protein, BLCA-4. Clin Cancer Res 6: 2618–2625, 2000; Rotem D, Cassel A, Lindenfeld N, et al: Urinary cytokeratin 20 as a marker for transitional cell carcinoma. Eur Urol 37: 601–604, 2000; Sanchez-Carbayo M, Urrutia M, Gonzalez de Buitrago J M, et al: Evaluation of two new urinary tumor markers: bladder tumor fibronectin and cytokeratin 18 for the diagnosis of bladder cancer. Clin Cancer Res. 6: 3585–3594, 2000; Sanchez-Carbayo M, Urrutia M, Silva J M, et al; Urinary tissue polypeptide-specific antigen for the diagnosis of bladder cancer. Urology 55: 526–532, 2000; Smith S D, Wheeler M A, Plescia J, et al: Urine detection of survivin and diagnosis of bladder cancer. JAMA 285: 324–328, 2001.

However, to our knowledge, none of the above cited references have reported the expression of a human HURP gene in bladder cancer or urothelial cancer. It is surprisingly found by the applicant that TCC tissue samples displayed reproducible and significant expression of HURP mRNA transcripts. Based on this finding, it is possible to develop an accurate, convenient and noninvasive diagnostic method for the detection, preliminary screening or monitoring of bladder cancer in a human subject by analyzing the expression of a human HURP gene in a biological sample, such as tumor tissue samples and voided urine, the detected expression of the human HURP gene being indicative of the presence of the bladder cancer.

SUMMARY OF THE INVENTION

Therefore, in the first aspect of this invention, the present invention provides a method for the detection of bladder cancer in a human subject, comprising the steps of:

obtaining a biological sample taken from a subject suspected to have bladder cancer; and detecting the expression of a human HURP gene in said sample, the detected expression of the human HURP gene being indicative of the presence of the bladder cancer.

In the second aspect, the present invention provides a method for monitoring bladder cancer in a human subject, comprising the steps of:

periodically obtaining a biological sample taken from a subject suspected to have bladder cancer; and detecting the expression of a human HURP gene in said sample, the detected expression of the human HURP gene being indicative of the presence of the bladder cancer.

In a third aspect, the present invention provides a primer set for the detection of bladder cancer in a human subject, comprising a forward primer having a nucleotide sequence selected from the sequences as set forth in SEQ ID NO:2 and SEQ ID NO:4, and a reverse primer having a nucleotide sequence selected from the sequences as set forth in SEQ ID NO:3 and SEQ ID NO:5.

In a fourth aspect, the present invention provides a diagnosis kit for the detection of bladder cancer in a human subject, containing at least a primer pair of a forward primer and a reverse primer, each primer having a nucleotide sequence that hybridizes to at least 13 nucleotides of a human HURP gene having a nucleotide sequence corresponding to SEQ ID NO:1.

The above and other objects, features and advantages of the present invention will become apparent with reference to the following detailed description and the preferred examples that accompany the appended Drawings, of which:

DETAILED DESCRIPTION OF THE INVENTION

Genes and proteins involved in cell cycle regulation and apoptosis have been found to be important in the development of cancers. There is a continuing need in the art for identification of components of cells which control the cell cycle and apoptosis.

The human hepatoma up-regulated protein (HURP) gene (NCBI accession no. AB076695) having a full length nucleotide sequence as set forth in SEQ ID NO:1 was first identified by Chen-Kung Chou at al. in hepatoma studies as a novel cancer-related gene involved in cell growth. In Chuo's research of hepatocellular carcinoma (HCC), a novel cell cycle regulated gene (CCRG) was identified as hepatoma up-regulated protein (HURP) from the search for novel genes specifically presented in cDNA libraries of human HCC tissues and cell-cycle dependent expression profile in microarray databases. (Chou et al., manuscript submitted for publication).

Surprisingly, the applicant, for the first time, found that the human HURP gene may be a powerful molecular maker for bladder cancer, and that the human HURP gene may be used in a non-invasive urinary diagnosis test that is sensitive enough to detect low-grade bladder tumors and specific to exclude a greater portion of patients with noncancerous or clinically insignificant conditions.

According to this invention, there is provided a method for the detection, preliminary screening or monitoring of bladder cancer in a human subject, comprising the steps of:

obtaining a biological sample taken from a subject suspected to have bladder cancer; and detecting the expression of a human HURP gene in said sample, the detected expression of the human HURP gene being indicative of the presence of the bladder cancer.

The present method can be applied in the detection, preliminary screening and monitoring of transitional cell carcinoma (TCC) of the bladder.

Preferably, the present method is carried out using a biological sample comprising cells selected from the group consisting of urothelial cancer cells, bladder cancer cells or a combination of both.

Preferably, the biological sample is selected from the group consisting of urine, urothelial biopsy, blood, plasma and serum. In a preferred embodiment of this invention, the biological sample is urine.

Figure 1:
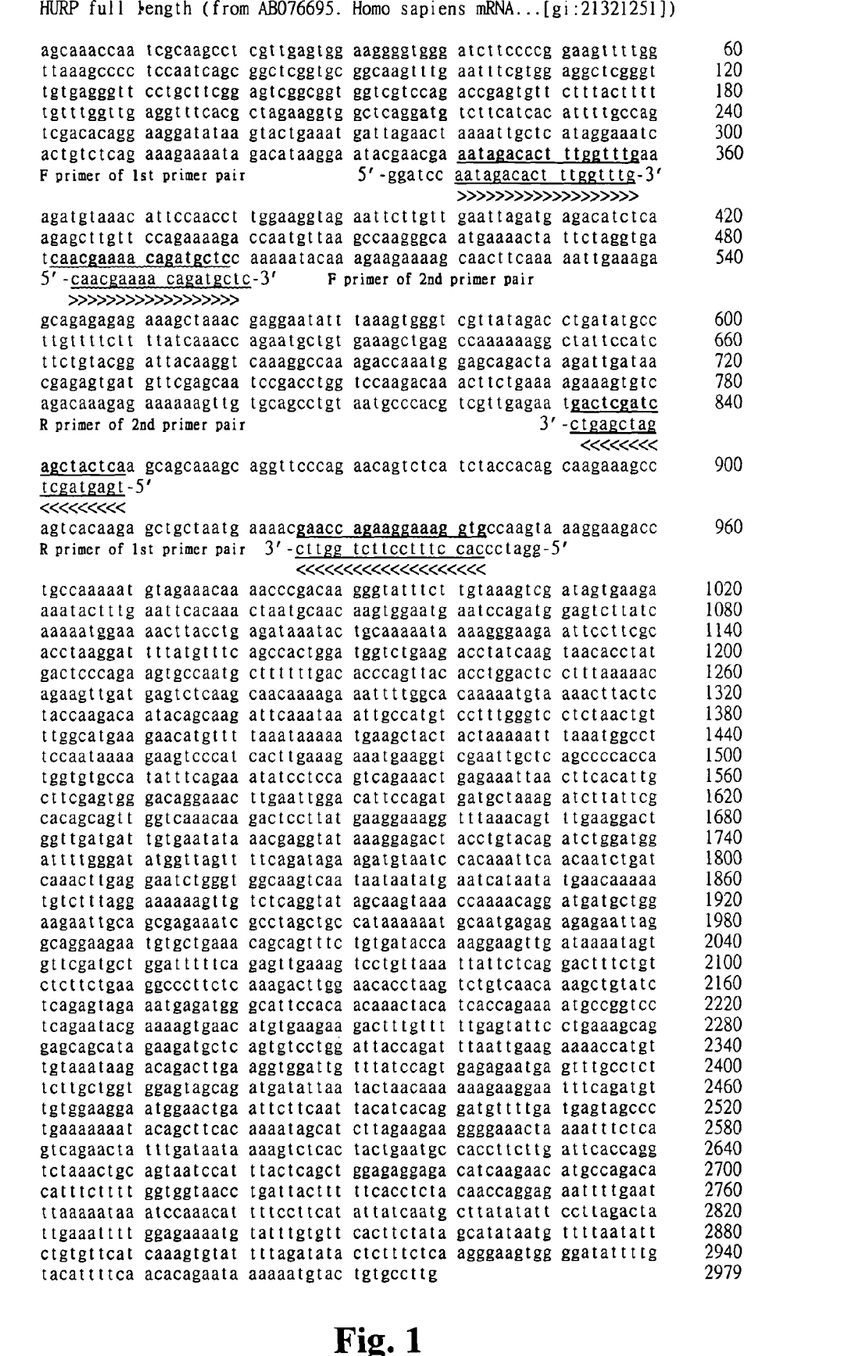
FIG. 1 shows the full length of nucleotide sequence of the human HURP gene (SEQ ID NO:1), in which the nucleotide sequences complementary to the four primers designed according to this invention are underlined and boldfaced.

The human HURP gene has a nucleotide sequence as set forth in FIG. 1 and SEQ ID NO:1, based on which oligonucloetides that hybridize to at least 13 nucleotides of a human HURP gene, can be designed to serve as either a diagnostic probe or a primer for the detection of the expression of said gene, using conventional methodologies well known in the field of biotechnology.

Taking as an example, referring to FIG. 1, the applicant has designed four primers useful in the present method for the detection of bladder cancer, including:

```
First primer pair:
                                          (SEQ ID NO:2)
forward primer 1    5'-ggatccaatagacactttggtttg-3'

(SEQ ID NO:3)
reverse primer 1    5'-ggatcccacctttccttctggttc-3'

Second primer pair:
                                          (SEQ ID NO:4)
forward primer 2    5'-caacgaaaacagatgctc-3'

(SEQ ID NO:5)
reverse primer 2    5'-tgagtagctgatcgagtc-3'
```

It is contemplated that the forward primer 1 can be paired with the reverse primer 2, and the forward primer 2 can be paired with the reverse primer 1.

According to this invention, the expression of a human HURP gene is determined by analysis of an mRNA transcript from the human HURP gene or protein translated from mRNA transcript of the human HURP gene.

The detection of the translated protein from mRNA transcript of the human HURP gene may be conducted by conventional methodologies well known in the field of biotechnology.

In a preferred embodiment of this invention, the detection of the expression of the human HURP gene is conducted by detecting the presence of mRNA transcript of the human HURP gene in the biological sample.

Preferably, the detection of the presence of mRNA transcript of the human HURP gene is conducted using at least one of the following methodologies: hybridization, cycling probe reaction, polymerase chain reaction (PCR), nested PCR, reverse-transcriptase polymerase chain reaction (RT-PCR), multiplex PCR polymerase chain reaction-single strand conformation polymorphism, ligase chain reaction (LCR), restriction fragments length polymorphism nucleic acid sequence-based amplification (NASBA), and transcription-mediated amplification (TMA).

In a preferred embodiment of this invention, the detection of the presence of mRNA transcript of the human HURP gene is conducted using RT-PCR.

In a more preferred embodiment of this invention, the detection of the presence of mRNA transcript of the human HURP gene is conducted by:

(a) extracting total RNA from the biological sample;
(b) subjecting the extracted RNA from step (a) to a reverse transcriptase-polymerase chain reaction (RT-PCR) treatment using at least a primer pair of a forward primer and a reverse primer, each primer having a nucleotide sequence that hybridizes to at least 13 nucleotides of a human HURP gene having a nucleotide sequence corresponding to SEQ ID NO:1; and
(c) detecting whether or not a RT-PCR product having a nucleotide sequence identical or complementary to a part of the nucleotide sequence of the human HURP gene has been produced from the RT-PCR treatment of step (b), the presence of said RT-PCR product being indicative of the presence of the bladder cancer.

Preferably, each of the primers used in step (b) hybridizes to at least 18 nucleotides of the human HURP gene.

Preferably, the at least a primer pair used in step (b) comprises a forward primer having a nucleotide sequence selected from the sequences as set forth in SEQ ID NO:2 and SEQ ID NO:4, and a reverse primer having a nucleotide sequence selected from the sequences as set forth in SEQ ID NO:3 and SEQ ID NO:5.

In a preferred embodiment of this invention, the at least a primer pair used in step (b) comprises a forward primer having a nucleotide sequence corresponding to SEQ ID NO:4 and a reverse primer having a nucleotide sequence corresponding to SEQ ID NO:5.

In a preferred embodiment of this invention, the RT-PCR treatment in step (b) includes a first amplification reaction using a first primer pair comprising a first forward primer having a nucleotide sequence corresponding to SEQ ID NO:2 and a first reverse primer having a nucleotide sequence corresponding to SEQ ID NO:3, and a second amplification reaction using a second primer pair comprising a second forward primer having a nucleotide sequence corresponding to SEQ ID NO:4 and a second reverse primer having a nucleotide sequence corresponding to SEQ ID NO:5.

According to this invention, there is provided a primer set for the detection of bladder cancer in a human subject, comprising a forward primer having a nucleotide sequence selected from the sequences as set forth in SEQ ID NO:2 and SEQ ID NO:4, and a reverse primer having a nucleotide sequence selected from the sequences as set forth in SEQ ID NO:3 and SEQ ID NO:5.

In a preferred embodiment of this invention, the forward primer has the nucleotide sequence as set forth in SEQ ID NO:2.

In another preferred embodiment of this invention, the forward primer has the nucleotide sequence as set forth in SEQ ID NO:4.

In a preferred embodiment of this invention, the reverse primer has the nucleotide sequence as set forth in SEQ ID NO:3.

In another preferred embodiment of this invention, the reverse primer has the nucleotide sequence as set forth in SEQ ID NO:5.

According to this invention, there is provided a diagnosis kit for the detection of bladder cancer in a human subject, containing at least a primer pair of a forward primer and a reverse primer, each primer having a nucleotide sequence that hybridizes to at least 13 nucleotides of a human HURP gene having a nucleotide sequence corresponding to SEQ ID NO:1.

In another preferred embodiment of this invention, the diagnosis kit contains a first primer pair comprising a first forward primer having a nucleotide sequence corresponding to SEQ ID NO:2 and a first reverse primer having a nucleotide sequence corresponding to SEQ ID NO:3, and a second primer pair comprising a second forward primer having a nucleotide sequence corresponding to SEQ ID NO:4 and a second reverse primer having a nucleotide sequence corresponding to SEQ ID NO:5.

In addition to the aforesaid, those skilled in the art will realize that a variety of applications within the scope of the present invention comprise using evaluating assays of any type.

For example, RNA and protein can be isolated and assayed from a test sample using techniques known in the art. They can, for example, be isolated from fresh or frozen biopsy, from formalin-fixed tissue, and from body fluids, such as blood, plasma, serum, urine, or sputum.

While RT-PCR can be used, other techniques are also contemplated. These include other techniques for assaying for specific mRNA species, including PCR, nested-PCR in situ-hybridization, Northern Blotting, high density expression array, micro array, as well as techniques for assaying for particular protein products, such as ELISA, Western Blotting and enzyme assays.

The present invention will be described in more detail with reference to the following examples, which are given for the purpose of illustration only and are not intended to limit the scope of the present invention.

EXAMPLE 1

RT-PCR Analysis of HURP Gene Expression

Materials and Methods:

Patient Characteristics

Eighty TCC samples from urinary tracts were obtained using cystectomy and transurethral resection in Chi Mei Medical Center from March 1998 through September 2001. Remote grossly normal tissues were also obtained for the analysis and they were regarded as the tumor-adjacent tissue samples. All tissue samples were frozen in liquid nitrogen and stored for varying periods at −86° C. Representative sections of each frozen block were embedded in paraffin and stained with hematoxylin-eosin and reviewed by a pathologist to assess the status of the tumors within the samples.

All specimens were graded using a modification of the World Health Organization classification and the pathological staging was according to the TNM pathological staging system (Epstein J I, Amin M B, Reuter V R, et al: *The World Health Organization/International Society of Urological Pathology consensus classification of urothelial (transitional cell) neoplasms of the urinary bladder. Bladder Consensus Conference Committee. Am J Surg Pathol* 22: 1435–1448, 1998; and Chisholm G D, Hindmarsh J R, Howatson A G, et al: *TNM* (1978) *in bladder cancer: use and abuse. Br J Urol* 52: 500–505, 1980).

Stages of a bladder tumor indicate how deeply the tumor has penetrated. Superficial tumors are termed Ta, and T1–4 are used to describe increasing degrees of penetration into the muscle. The grade of a bladder tumor is expressed on a scale of I–IV (1–4). The grade reflects the cytological appearance of the cells, in which Grade I cells are almost normal, Grade II cells are slightly deviant, Grade III cells are clearly abnormal, and Grade IV cells are highly abnormal.

RNA Isolation:

Total RNA was isolated from frozen tissue specimens or urine pellets using the Ultraspec™ RNA isolation system (Biotecx Laboratories Inc., Houston, Tex.). Approximately 0.5–1.0 gram of tissue was homogenized with 1 ml Ultraspec™ reagent in a handheld glass-Teflon. Subsequent to homogenization, the homogenate was stored at 4° C. for 5 minutes and then extracted with 0.2 ml of chloroform, followed by centrifugation at 12,000 g (4° C.) for 15 minutes. RNA in the aqueous phase was precipitated with an equal volume of isopropanol and washed twice with 75% ethanol. The content of the RNA was assessed (1 OD of A260 equals to 40 μg/ml RNA) spectrophotometrically, and the purity of extraction was assessed using the A260/280 ratio, which in all cases was above 1.75. For urine collection, 50 milliliters of clean-catch urine was obtained from every patient at the first voiding of the day. Samples were centrifuged at 3,000 g (4° C.) for 20 minutes, cell pellets were mixed with 1 ml Ultraspec™ reagent, and extracted using the same method as described above.

Reverse Transcriptase-Polymerase Chain Reaction

Single-strand complementary DNA (cDNA) was synthesized using oligo-dT priming of 1 μg of total RNA with 1 μl SuperScript II reverse transcriptase (Life Technologies Inc., Gaithersburg, Md.) for 50 minutes at 42° C. After heating at 70° C. for 15 minutes, a first amplification reaction was carried out with one tenth of the reverse-transcribed RNA, Taq polymerase buffer containing 200 μmol/L dNTPs, 1 U DyNAzyme™ II DNA Polymerase (Finnzymes Inc., Finland), and 10 μM of each of the human HURP primers 5'-GGATCC<u>AATAGACACTTTGGTTTG</u>-3' (forward) and 5'-GGATCCCACCTTTCCTTCT<u>GGTTC</u>-3' (reverse), with denaturation at 94° C. for 1 minute, annealing at 55° C. for 1 minute, and extension at 72° C. for 1 minute for 30 cycles, followed by incubation at 72° C. for 5 minutes.

For nested PCR of the urine specimens, one tenth of the first amplification products was subjected to a second round of amplification with nested HURP primers 5'-CAAC-GAAAACAGATGCTC-3' (forward) and 5'-TGAGTAGCT-GATCGAGTC-3' (reverse), with denaturation at 94° C. for 1 minute, annealing at 60° C. for 1 minute, and extension at 72° C. for 1 minute for 30 cycles, followed by incubation at 72° C. for 5 minutes.

Figure 2:
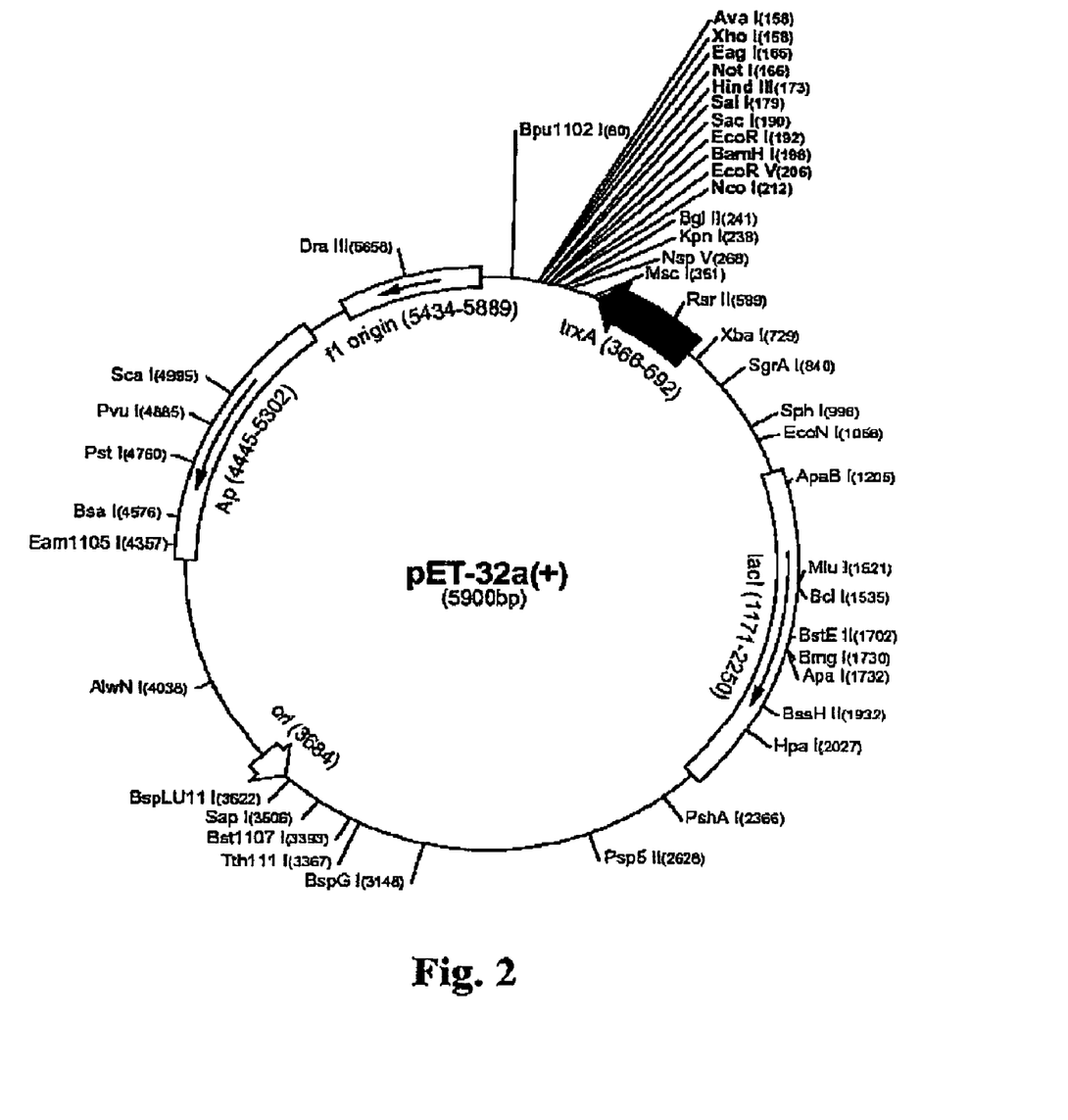
FIG. 2 shows the restriction map of a vector pET32a (Novagen Inc.) employed in the following Examples, wherein the BamH I restriction site is used to insert a full length nucleotide sequence of the human HURP gene.

Routine RT-PCR controls without RT as a template were negative, and with pET32a-HURP constructed as shown in FIG. 2 by inserting a full length HURP nucleotide sequence into a pET32a(+) vector (purchased from Novagen Inc.) as a template were positive. Amplified products were separated using electrophoresis with 0.1 μg GeneRuler™ 100 bp DNA Ladder (MBI Fermentas, Lithuania) in 1.5% agarose gels and visualized using ethidium bromide staining.

Quantification and Normalization of Data

To quantify the mRNA expression levels of HURP gene, all gels were photographed with the Image Master™ VDS video imaging system (Amersham Pharmacia Biotech Inc., Piscataway), and documented using LISCAP image capture software (Amersham Pharmacia Biotech Inc., version 1.0). The optical pixels of PCR products were quantified to arbitrary units using ImageMaster™ TotalLab Software (Amersham Pharmacia Biotech Inc., version 1.11).

In order to compare the tested samples, normalization of the data was necessary. For this purpose, the PCR amplified products of β-actin were used as an internal standard to represent the relatively equal amounts of cDNA template subjected to PCR. The mean values were expressed as mean±SD and were compared using the Student's t test.

Figure 3A:
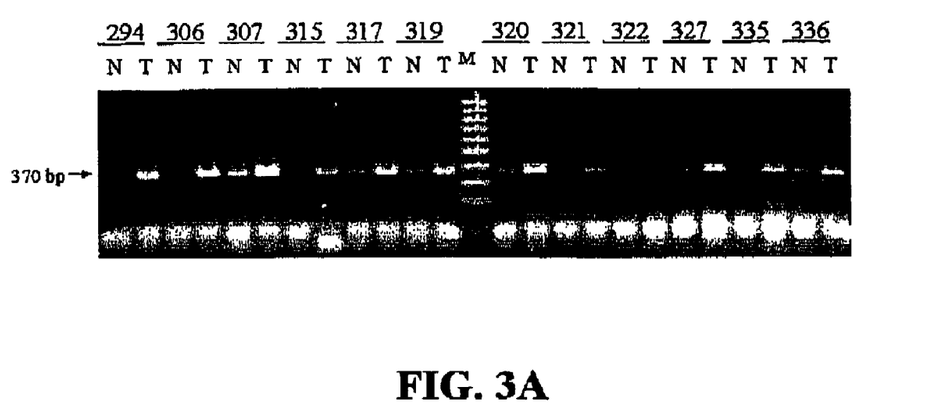
FIGS. 3A and 3B respectively show the RT-PCR analysis of the expression of HURP and β-actin in TCC tissues, in which N=tumor-adjacent tissue, T=tumor tissue, and 294, 306, 307, 315, 317, 319, 320, 321, 322, 327, 335 and 337=patient numbers.
Figure 3B:
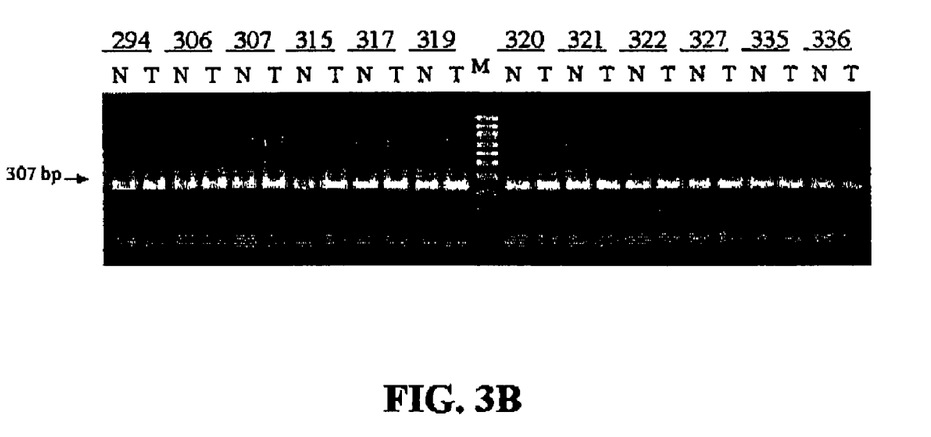

Results:

The representative expression patterns of HURP gene in TCC tissue samples and control subjects are shown in FIG. 3A. Relatively more mRNA transcripts of the human HURP gene were amplified in tumor parts of 11 pairs (patient number: 294N/T, 306N/T, 307N/T, 315 N/T, 317 N/T, 319 N/T, 320 N/T, 321 N/T, 327 N/T, 335 N/T, 337 N/T) than tumor-adjacent parts (see FIG. 3A). Only one pair of tissue samples (patient number: 322 N/T) both showed undetectable transcripts of the human HURP gene. As an internal standard, the PCR amplified products of β-actin (see FIG. 3B) was used to represent the relatively equal amounts of cDNA template subjected to PCR.

EXAMPLE 2

Evaluation of Tumor Specificity of HURP Gene Expression by RT-PCR Analysis

In order to determine whether the over-expression of HURP exhibited tumor specificity, the human HURP transcripts of prostatic urothelium from benign prostatic hyperplasia (BPH) patients were amplified using reverse transcriptase-polymerase chain reaction (RT-PCR).

The experiments were conducted according to the procedures as set forth in the above Example 1, except that HURP transcripts of prostatic urothelium from benign prostatic hyperplasia (BPH) patients were amplified using reverse transcriptase-polymerase chain reaction (RT-PCR) to determine whether HURP gene expression exhibited tumor specificity.

Figure 4:
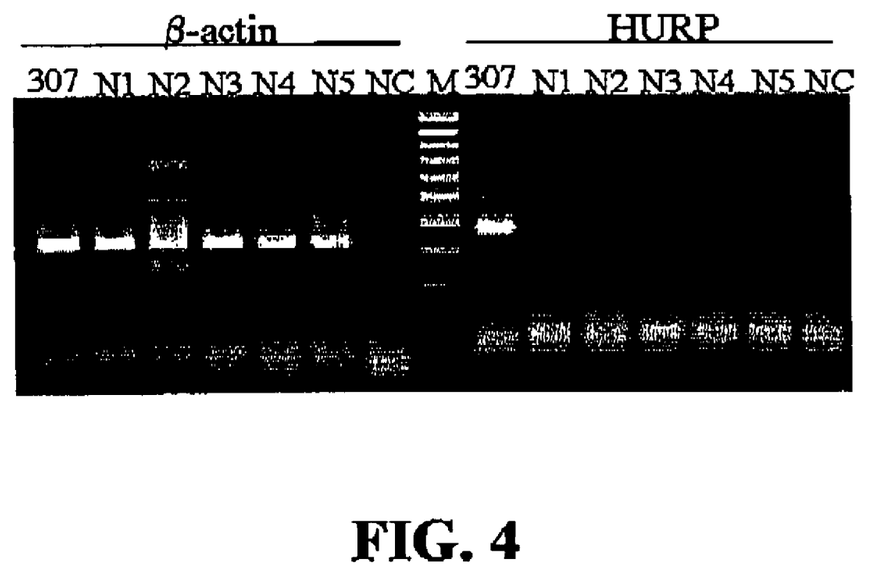
FIG. 4 shows the RT-PCR analysis of the human HURP expression in prostatic urothelium samples taken from five benign prostatic hyperplasia patients, in which left: β-actin (307 bp) and right HURP (370 bp); N1, N2, N3, N4 and N5=5 benign prostatic hyperplasia (BPH) samples; NC=negative control; and M indicates molecular weight markers in base pair.

15 specimens of prostatic urothelium from BPH patients with normal cytoscopy were collected and subjected to RT-PCR. Referring to FIG. 4, the β-actin transcripts were equally amplified from five representative samples of BPH urothelium, but no HURP transcripts were detected in these samples. In addition to the BPH samples, non-bladder controls, including four samples from the liver and four samples from the heart, were tested and no HURP transcripts were detected in these tissues (data not shown).

EXAMPLE 3

Tumor Stage Evaluation by RT-PCR Analysis of HURP Gene Expression

In order to determine the possible correlation between the over-expression of HURP gene and the tumor grade, the human HURP transcripts of 45 pairs of tissue samples comprising a TCC and a counterpart of tumor-adjacent tissue samples were analyzed, and normalized with β-actin transcripts.

Referring to Table 1, it is noted that 35 tumor-adjacent parts (35/45, 77.8%) expressed less amounts of HURP gene than tumor parts (Group I, p<0.0001), and 10 tumor-adjacent parts (10/45, 22.2%) displayed nearly equal amounts of HURP gene to tumor parts (Group 2).

Eighty TCC patients with pathological identification of zero grade I, 37 grade II, 31 grade III and 12 grade IV were collected, and the human HURP expression ratios of the tissue samples are listed in Table II. It appears that no significant correlation is present between HURP expression and tumor grade. In those nine tumors with HURP-negative, six were grade II, one was grade III and two were grade IV.

TABLE I

HURP expression ratio of TCC tumor and tumor-adjacent tissues

| Group | No. | HURP expression ratio* (Normalized with β-actin) Mean ± SD | |
|---|---|---|---|
| | | TCC Tumor | Tumor-adjacent |
| I | 35 | 0.658 ± 0.061 | 0.070 ± 0.085† |
| II | 10 | 0.820 ± 0.275 | 0.770 ± 0.327 |

*HURP over β-actin (fold of optical pixels)
†P < 0.0001

TABLE II

HURP expression ratio of TCC patients

| Patient characteristics | No. | HURP-positive (%) | HURP-negative (%) | HURP expression ratio (Normalized with β-actin) Mean ± SD |
|---|---|---|---|---|
| TCC, Grade I | 0 | — | — | — |
| TCC, Grade II | 37 | 31/37 (83.8) | 6/37 (16.2) | 0.66 ± 0.394 |
| TCC, Grade III | 31 | 30/31 (96.8) | 1/31 (3.2) | 0.59 ± 0.309 |
| TCC. Grade IV | 12 | 10/12 (83.3) | 2/10 (16.7) | 0.54 ± 0.129 |
| Total | 80 | 71/80 (88.8) | 9/60 (11.2) | 0.55 ± 0.369 |

EXAMPLE 4

Evaluation of HURP Gene Expression as a Biomarker for the Detection of TCC

Figure 5A:
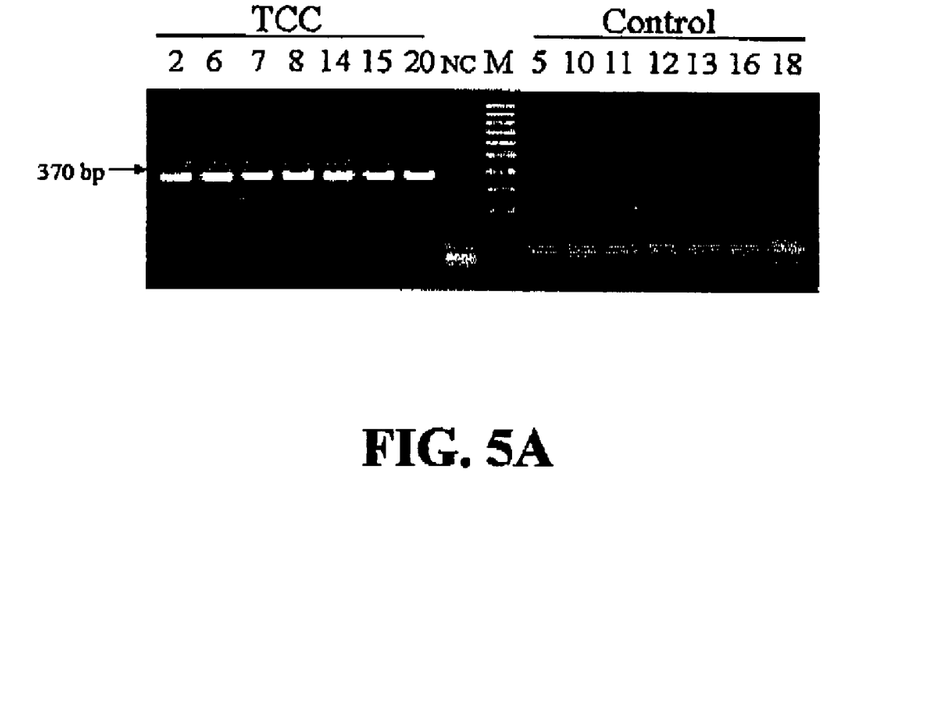
FIGS. 5A and 5B respectively show the RT-PCR analysis of the expression of HURP and β-actin in voided urine samples, in which 2, 6, 7, 8, 14, 15, 20, 5, 10, 11, 12, 13, 16 and 18=patient numbers; NC: negative control; M indicates molecular weight markers in base pair.
Figure 5B:
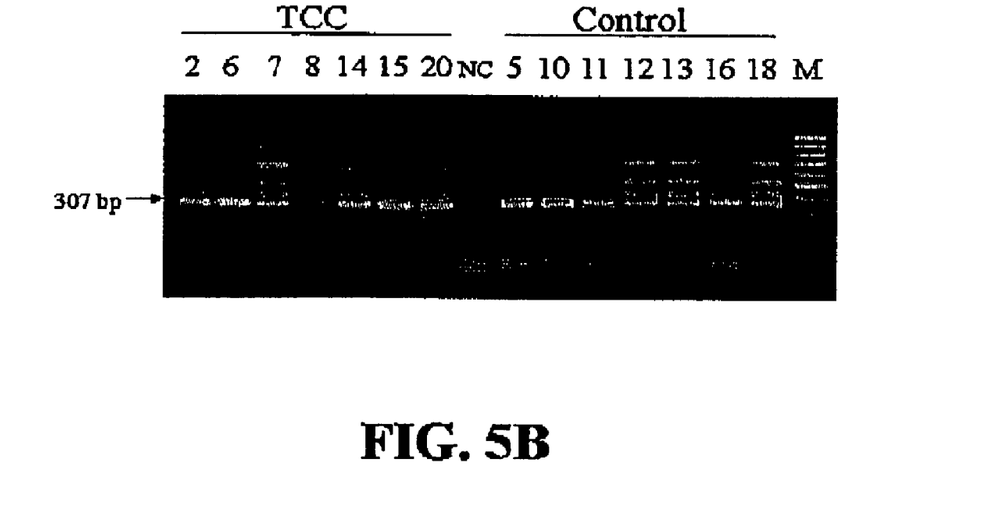

In order to evaluate the potential applicability of urine-HURP as a novel urine molecular marker for the detection of urinary TCC, seven additional patients with new or recurrent TCC were analyzed for urine-HURP using RT-PCR. Total RNA was extracted from urine cell pellets and reverse-transcribed by oligo-dT priming. Amplification reactions were carried out with HURP-specific primers or β-actin-specific primers. A 370-base pair cDNA was amplified from urine cell pellets of all the patients with TCC (FIG. 5A). In contrast, urine cell pellets from seven additional individuals (B3 had urinary tract infection, 2 had chronic inflammation of the urinary bladder, 1 had renal cell carcinoma, and 1 had BPH) had no HURP transcripts. In controlled experiments, a 307-base pair β-actin-cDNA fragment was indistinguishably amplified from urine of control subjects and patients with TCC (FIG. 5B).

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A method for the detection of bladder cancer in a human subject, comprising the steps of:
   (1) obtaining a biological sample from a subject suspected to have bladder cancer; wherein the biological sample is selected from the group-consisting of urine, a urothelial biopsy and a combination thereof, and
   (2) detecting the expression of a human hepatoma up-regulated protein (HURP) gene in said sample by detecting the presence of mRNA transcript of the human HURP gene in said sample, the detected expression of the human HURP gene being indicative of the presence of the bladder cancer.

2. The method according to claim 1, wherein the bladder cancer is transitional cell carcinoma (TCC) of the bladder.

3. The method according to claim 1, wherein the biological sample comprises urothelial cancer cells.

4. The method according to claim 1, wherein the biological sample is urine.

5. The method according to claim 1, wherein the human HURP gene has the nucleotide sequence of SEQ ID NO: 1.

6. The method according to claim 5 wherein the detection of the presence of mRNA transcript of the human HURP gene is conducted using at least one of the following methodologies: hybridization, cycling probe reaction, polymerase chain reaction (PCR), nested PCR, reverse-transcriptase polymerase chain reaction (RT-PCR), multiplex PCR, polymerase chain reaction-single strand conformation polymorphism, ligase chain reaction (LCR), restriction fragment length polymorphism, nucleic acid sequence-based amplification (NASBA), and transcription-mediated amplification (TMA).

7. The method according to claim 1, wherein the detection of the presence of mRNA transcript of the human HURP gene is conducted using RT-PCR.

8. The method according to claim 1, wherein the detection of the presence of mRNA transcript of the human HURP gene is conducted by:
   (a) extracting total RNA from the biological sample;
   (b) subjecting the extracted RNA from step (a) to a reverse transcriptase-polymerase chain reaction (RT-PCR) treatment using at least a primer pair of a forward primer and a reverse primer, each primer having a nucleotide sequence that hybridizes to at least 13 contiguous nucleotides of a human HURP gene having a nucleotide sequence comprising SEQ ID NO:1; and
   (c) detecting whether or not a RT-PCR product having a nucleotide sequence identical or complementary to a part of the nucleotide sequence of the human HURP gene has been produced from the RT-PCR treatment of step (b), the presence of said RT-PCR product being indicative of the presence of the bladder cancer.

9. The method according to claim 8, wherein the at least a primer pair used in step (b) comprises a forward primer having the nucleotide sequence selected from the sequences of SEQ ID NO: 2 and SEQ ID NO: 4, and a reverse primer having the nucleotide sequence selected from the sequences of SEQ ID NO: 3 and SEQ ID NO: 5.

10. The method according to claim 8, wherein the at least a primer pair used in step (b) comprises a forward primer having a nucleotide sequence comprising SEQ ID NO:4 and a reverse primer having a nucleotide sequence comprising SEQ ID NO:5.

11. The method according to claim 8, wherein the RT-PCR treatment in step (b) includes a first amplification reaction using a first primer pair comprising a first forward primer having a nucleotide sequence comprising SEQ ID NO:2 and a first reverse primer having a nucleotide sequence comprising SEQ ID NO:3, and a second amplification reaction using a second primer pair comprising a second forward primer having a nucleotide sequence comprising SEQ ID NO:4 and a second reverse primer having a nucleotide sequence comprising SEQ ID NO:5.

12. A method for monitoring bladder cancer in a human subject, comprising the steps of:
   (1') periodically obtaining a biological sample from a subject suspected to have bladder cancer; wherein the biological sample is selected from the group consisting of urine, a urothelial biopsy and a combination thereof; and
   (2') detecting the expression of a human HURP gene in said sample by detecting the presence of mRNA transcript or the human HURP gene in said sample, the detected expression of the human HURP gene being indicative of the presence of the bladder cancer.

13. The method according to claim 12, wherein the bladder cancer is transitional cell carcinoma (TCC) of the bladder.

14. The method according to claim 12, wherein the biological sample comprises urothelial cancer cells.

15. The method according to claim 12, wherein the biological sample is urine.

16. The method according to claim 12, wherein the human HURP gene has the nucleotide sequence of SEQ ID NO: 1.

17. The method according to claim 12, wherein the detection of the presence of mRNA transcript of the human HURP gene is conducted using at least one of the following methodologies: hybridization, cycling probe reaction, polymerase chain reaction (PCR), nested PCR, reverse-transcriptase polymerase chain reaction (RT-PCR), multiplex PCR, polymerase chain reaction-single strand conformation polymorphism, ligase chain reaction (LCR), restriction fragments length polymorphism, nucleic acid sequence-based amplification (NASBA), and transcription-mediated amplification (TMA).

18. The method according to claim 12, wherein the detection of the presence of mRNA transcript of the human HURP gene is conducted using RT-PCR.

19. The method according to claim 12, wherein the detection of the presence of mRNA transcript of the human HURP gene is conducted by:
   (a') extracting total RNA from the biological sample;
   (b') subjecting the extracted RNA from step (a') to a reverse transcriptase-polymerase chain reaction (RT-PCR) treatment using at least a primer pair of a forward primer and a reverse primer, each primer having a nucleotide sequence that hybridizes to at least 13 contiguous nucleotides of a human HURP gene having a nucleotide sequence comprising SEQ ID NO:1; and
   (c') detecting whether or not a RT-PCR product having a nucleotide sequence identical or complementary to a part of the nucleotide sequence of the human HURP gene has been produced from the RT-PCR treatment of step (b'), the presence of said RT-PCR product being indicative of the presence of the bladder cancer.

20. The method according to claim 19, wherein the at least a primer pair used in step (b') comprises a forward primer having the nucleotide sequence selected from the sequences of SEQ ID NO: 2 and SEQ ID NO: 4, and a reverse primer having the nucleotide sequence selected from the sequences of SEQ ID NO: 3 and SEQ ID NO: 5.

21. The method according to claim 19, wherein the at least a primer pair used in step (b') comprises a forward primer having a nucleotide sequence comprising SEQ ID NO:4 and a reverse primer having a nucleotide sequence comprising SEQ ID NO:5.

22. The method according to claim 19, wherein the RT-PCR treatment in step (b') includes a first amplification reaction using a first primer pair comprising a first forward primer having a nucleotide sequence comprising SEQ ID NO:2 and a first reverse primer having a nucleotide sequence comprising SEQ ID NO:3, and a second amplification reaction using a second primer pair comprising a second forward primer having a nucleotide sequence comprising SEQ ID NO:4 and a second reverse primer having a nucleotide sequence comprising SEQ ID NO:5.

* * * * *

SEQUENCE LISTING

<160> NUMBER OF SEQ ID NOS: 5

<210> SEQ ID NO 1
<211> LENGTH: 2979
<212> TYPE: DNA
<213> ORGANISM: Homo Sapiens

<400> SEQUENCE: 1

| | | | | | |
|---|---|---|---|---|---|
| agcaaaccaa | tcgcaagcct | cgttgagtgg | aagggtgggg | atcttcccg | gaagttttgg | 60 |
| ttaaagcccc | tccaatcagc | ggctcggtgc | ggcaagtttg | aatttcgtgg | aggctcgggt | 120 |
| tgtgagggtt | cctgcttcgg | agtcggcggt | ggtcgtccag | accgagtgtt | ctttactttt | 180 |
| tgtttggttg | aggtttcacg | ctagaaggtg | gctcaggatg | tcttcatcac | attttgccag | 240 |
| tcgacacagg | aaggatataa | gtactgaaat | gattagaact | aaaattgctc | ataggaaatc | 300 |
| actgtctcag | aaagaaaata | gacataagga | atacgaacga | aatagacact | ttggtttgaa | 360 |
| agatgtaaac | attccaacct | tggaaggtag | aattcttgtt | gaattagatg | agacatctca | 420 |
| agagcttgtt | ccagaaaaga | ccaatgttaa | gccaagggca | atgaaaacta | ttctaggtga | 480 |
| tcaacgaaaa | cagatgctcc | aaaaatacaa | agaagaaaag | caacttcaaa | aattgaaaga | 540 |
| gcagagagag | aaagctaaac | gaggaatatt | taaagtgggt | cgttatagac | ctgatatgcc | 600 |
| ttgtttttctt | ttatcaaacc | agaatgctgt | gaaagctgag | ccaaaaaagg | ctattccatc | 660 |
| ttctgtacgg | attacaaggt | caaaggccaa | agaccaaatg | gagcagacta | agattgataa | 720 |
| cgagagtgat | gttcgagcaa | tccgacctgg | tccaagacaa | acttctgaaa | agaaagtgtc | 780 |
| agacaaagag | aaaaaagttg | tgcagcctgt | aatgccacg | tcgttgagaa | tgactcgatc | 840 |
| agctactcaa | gcagcaaagc | aggttcccag | aacagtctca | tctaccacag | caagaaagcc | 900 |
| agtcacaaga | gctgctaatg | aaaacgaacc | agaaggaaag | gtgccaagta | aggaagacc | 960 |
| tgccaaaaat | gtagaaacaa | acccgacaa | gggtatttct | tgtaaagtcg | atagtgaaga | 1020 |
| aaatactttg | aattcacaaa | ctaatgcaac | aagtggaatg | aatccagatg | gagtcttatc | 1080 |
| aaaaatggaa | aacttacctg | agataaatac | tgcaaaaata | aagggaaga | attccttcgc | 1140 |
| acctaaggat | tttatgtttc | agccactgga | tggtctgaag | acctatcaag | taacacctat | 1200 |
| gactcccaga | agtgccaatg | cttttttgac | acccagttac | acctggactc | ctttaaaaac | 1260 |
| agaagttgat | gagtctcaag | caacaaaaga | aattttggca | caaaaatgta | aaacttactc | 1320 |
| taccaagaca | atacagcaag | attcaaataa | attgccatgt | cctttgggtc | ctctaactgt | 1380 |
| ttggcatgaa | gaacatgttt | taaataaaaa | tgaagctact | actaaaaatt | taaatggcct | 1440 |
| tccaataaaa | gaagtcccat | cacttgaaag | aaatgaaggt | cgaattgctc | agccccacca | 1500 |
| tggtgtgcca | tatttcagaa | atatcctcca | gtcagaaact | gagaaattaa | cttcacattg | 1560 |
| cttcgagtgg | gacaggaaac | ttgaattgga | cattccagat | gatgctaaag | atcttattcg | 1620 |
| cacagcagtt | ggtcaaacaa | gactccttat | gaaggaaagg | tttaaacagt | tgaaggact | 1680 |
| ggttgatgat | tgtgaatata | acgaggtat | aaaggagact | acctgtacag | atctggatgg | 1740 |
| atttttgggat | atggttagtt | ttcagataga | agatgtaatc | cacaaattca | acaatctgat | 1800 |
| caaacttgag | gaatctgggt | ggcaagtcaa | taataatatg | aatcataata | tgaacaaaaa | 1860 |
| tgtctttagg | aaaaaagttg | tctcaggtat | agcaagtaaa | ccaaaacagg | atgatgctgg | 1920 |
| aagaattgca | gcgagaaatc | gcctagctgc | cataaaaaat | gcaatgagag | agagaattag | 1980 |
| gcaggaagaa | tgtgctgaaa | cagcagtttc | tgtgatacca | aaggaagttg | ataaaatagt | 2040 |

```
gttcgatgct ggatttttca gagttgaaag tcctgttaaa ttattctcag gactttctgt    2100
ctcttctgaa ggcccttctc aaagacttgg aacacctaag tctgtcaaca aagctgtatc    2160
tcagagtaga aatgagatgg gcattccaca acaaactaca tcaccagaaa atgccggtcc    2220
tcagaatacg aaaagtgaac atgtgaagaa gactttgttt ttgagtattc ctgaaagcag    2280
gagcagcata gaagatgctc agtgtcctgg attaccagat ttaattgaag aaaaccatgt    2340
tgtaaataag acagacttga aggtggattg tttatccagt gagagaatga gtttgcctct    2400
tcttgctggt ggagtagcag atgatattaa tactaacaaa aaagaaggaa tttcagatgt    2460
tgtggaagga atgaaactga attcttcaat tacatcacag gatgttttga tgagtagccc    2520
tgaaaaaaat acagcttcac aaaatagcat cttagaagaa ggggaaacta aaatttctca    2580
gtcagaacta tttgataata aaagtctcac tactgaatgc caccttcttg attcaccagg    2640
tctaaactgc agtaatccat ttactcagct ggagaggaga catcaagaac atgccagaca    2700
catttctttt ggtggtaacc tgattacttt ttcacctcta caaccaggag aattttgaat    2760
ttaaaaataa atccaaacat tttccttcat attatcaatg cttatatatt ccttagacta    2820
ttgaaatttt ggagaaaatg tatttgtgtt cacttctata gcatataatg ttttaatatt    2880
ctgtgttcat caaagtgtat tttagatata ctctttctca agggaagtgg ggatattttg    2940
tacattttca acacagaata aaaaatgtac tgtgccttg                          2979
```

<210> SEQ ID NO 2
<211> LENGTH: 24
<212> TYPE: DNA
<213> ORGANISM: Artificial sequence
<220> FEATURE:
<223> OTHER INFORMATION: amplification primer for HURP

<400> SEQUENCE: 2
ggatccaata gacactttgg tttg    24

<210> SEQ ID NO 3
<211> LENGTH: 24
<212> TYPE: DNA
<213> ORGANISM: Artificial sequence
<220> FEATURE:
<223> OTHER INFORMATION: amplification primer for HURP

<400> SEQUENCE: 3
ggatcccacc tttccttctg gttc    24

<210> SEQ ID NO 4
<211> LENGTH: 18
<212> TYPE: DNA
<213> ORGANISM: Artificial sequence
<220> FEATURE:
<223> OTHER INFORMATION: amplification primer for HURP

<400> SEQUENCE: 4
caacgaaaac agatgctc    18

<210> SEQ ID NO 5
<211> LENGTH: 18
<212> TYPE: DNA
<213> ORGANISM: Artificial sequence
<220> FEATURE:
<223> OTHER INFORMATION: amplification primer for HURP

<400> SEQUENCE: 5
tgagtagctg atcgagtc    18